United States Patent [19]

Hamamoto et al.

[11] Patent Number: 5,168,046
[45] Date of Patent: Dec. 1, 1992

[54] METHOD FOR DETERMINATION OF GLUCOSE CONCENTRATION

[75] Inventors: Katsumi Hamamoto, Otsu; Kazunori Hirose, Kyoto, both of Japan

[73] Assignee: Kyoto Daiichi Kagaku Co., Ltd., Kyoto, Japan

[21] Appl. No.: 548,367

[22] Filed: Jul. 5, 1990

[30] Foreign Application Priority Data

Jul. 13, 1989 [JP] Japan .................................. 1-180753

[51] Int. Cl.$^5$ ......................... C12Q 1/26; G01N 33/00
[52] U.S. Cl. ........................................ 435/14; 435/25; 436/95
[58] Field of Search ....................... 435/14, 25; 436/95

[56] References Cited

U.S. PATENT DOCUMENTS 4,547,280 10/1985 Karasawa et al. ..................... 435/22

OTHER PUBLICATIONS

Abstract of Japanese Patent Document 59-168371; Yumiko Abe et al; Sep. 22, 1984.
Extended Abstracts/Electrochemical Society, vol. 87, No. 2, 1987, p. 2276; Genshaw et al. "Whole Blood Glucose Enzyme Electrode".
Clin. Chem. vol. 25, No. 4, 1979, pp. 531-534; Meites et al.; "Preservation, Distribution, and Assay of Glucose in Blood, With Special Reference to the Newborn".
Biological Abstracts, vol. 82, No. 10, 1986, p. 605, T. Kanluan et al.; "Comparison of Plasma and Whole Blood Glucose Determination".

Primary Examiner—David M. Naff
Assistant Examiner—T. J. Reardon
Attorney, Agent, or Firm—Birch, Stewart, Kolasch & Birch

[57] ABSTRACT

There is provided a method for the determination of a glucose concentration in a whole blood utilizing a biosensor. A correction of the measured glucose concentration for dilution error introduced by the solid component of blood cells is calculated based on the change in glucose concentration measured before and after significant glucose has diffused from blood cells into the buffer used to dilute the sample. Thus, the need to centrifuge blood samples to obtain a cell-free serum sample for glucose determination is eliminated.

11 Claims, 4 Drawing Sheets

METHOD FOR DETERMINATION OF GLUCOSE CONCENTRATION

BACKGROUND OF THE INVENTION

1. Field of the Invention

The present invention relates to a method for the determination of glucose concentration in blood, especially in serum, such concentration is called the "blood sugar concentration". In particular, the present invention relates to a method for the quick determination of glucose concentration in whole blood with a minimum error.

2. Description of the Related Art

Determination of glucose concentration in blood is required in medical research and treatment of some medical conditions. Various methods for the determination of the glucose concentration in the blood have been proposed and are carried out.

Among these methods, the glucose concentration in the blood is generally determined with a biosensor. Such a method is called the Glucose Sensor Method. In the glucose oxidase biosensor method, a glucose oxidase (GOD) fixed membrane is used in combination with a hydrogen peroxide electrode.

The Glucose Sensor Method is widely used especially in diagnosis and monitoring of diabetes since the glucose concentration is detected with high sensitivity without any pretreatment of blood because of substrate specificity obtained by using the glucose oxidase as part of the detection method.

Such biosensor method used for the determination of the blood sugar concentration in the blood comprises steps of:

separating a supernatant (plasma or serum) from the blood by centrifugation, diluting the supernatant with a suitable buffer solution, reacting glucose, oxygen and water in the supernatant with the fixed glucose oxidase, measuring an amount of hydrogen peroxide produced by the enzyme reaction in terms of an output (current) of the hydrogen peroxide electrode, and determining a decomposition rate of glucose, that is, a production rate of hydrogen peroxide.

FIG. 1 schematically shows an apparatus used in the biosensor method for the determination of the glucose concentration in the serum. A cell 1 for the determination of the glucose concentration comprises a GOD fixed hydrogen peroxide electrode 2, and a liquid in the cell is thoroughly stirred with a stirrer 3 and a stirring member 4. A buffer solution is supplied in the cell through a valve 6 with a pump 5. After the determination, the liquid in the cell is discharged through a valve 8 with a pump 7. A sample to be determined is supplied in the cell with a sample 9.

The decomposition rate of glucose by the glucose oxidase is proportional to the glucose concentration in the buffer solution. However, the amount of the glucose decomposed is so small that the glucose concentration in the buffer solution is regarded to be constant. Thus, the hydrogen peroxide production rate is constant in a steady state. When the sample is supplied in the buffer solution, the output current from the hydrogen peroxide electrode is, for example, as shown in FIG. 2. The output current of the hydrogen peroxide electrode becomes constant after about 10 seconds from the sample supply.

A calibration curve is beforehand obtained which shows a relation between the glucose concentration and the output current of the hydrogen peroxide electrode after 10 to 20 seconds from the sample supply. Then, the glucose concentration the sample to be measured is obtained as follows: the output current of the hydrogen peroxide electrode with respect to the sample diluted with the buffer solution is measured; and the glucose concentration in the buffer solution which corresponds to the measured output current is read from the calibration curve. The glucose concentration in the diluted sample is converted to the glucose concentration in the undiluted sample by multiplying by the dilution ratio. This determination method is herein called the "Equilibrium Method".

When the glucose concentration in the sample is measured, the sample is usually diluted with the buffer solution as described above. The term "measured glucose concentration" is, hereinafter, intended to mean a glucose concentration which is the glucose concentration in the diluted sample. "Measured glucose concentration" is obtained from the measured output current by reading from a calibration curve plotted from output current measurements of some aqueous glucose solutions of known glucose concentration.

When the curve as shown in FIG. 2, namely, the curve which shows a relation between the output current (I) of the hydrogen peroxide electrode and time (t) is differentiated with respect to time (dI/dt), a curve as shown in FIG. 3 is obtained. A relative maximum value (i.e. a maximum changing rate of the hydrogen peroxide electrode output current) on the curve in FIG. 3 is proportional to the glucose concentration in the buffer solution. Thus, when a relation between the glucose concentration and the relative maximum value of dI/dt has been obtained beforehand as a calibration curve, the measured glucose concentration in a certain sample to be measured is obtained by measuring the relative maximum value of the changing rate of the output current of the hydrogen peroxide electrode immersed in the sample. This method to obtain the glucose concentration in the sample as described above is herein called the "First Differential Method". According to this method, the glucose concentration is obtained after 2 to 3 seconds from the supply of the sample into the buffer solution.

FIG. 4 shows a curve which results from a second order differentiation with time of the curve shown in FIG. 2 ($d^2I/dt^2$). A relative maximum value on the curve shown in FIG. is also proportional to the glucose concentration in the buffer solution. Thus, the glucose concentration in the buffer solution can be determined from the relative maximum value as in the First Differential Method. This method as just described above is called the "Second Differential Method". According to this method, the glucose concentration can be advantageously obtained in a shorter time than in the First Differential Method.

Broken lines in FIGS. 2 and 3 and dashed lines in FIGS. 3 and 4 each indicate correspondency of time as shown with arrows.

The glucose concentration obtained by any of the methods as described above is that in a homogeneous solution, for example the buffer solution in which the serum is diluted. Therefore, the serum must be obtained by previously separating blood cells from the blood by centrifugation. It takes about 10 to 15 minutes to centrifugally separate the serum. As long as such separation is required, a quick determination of the glucose concentration is impossible.

The biosensor method is preferably applied to whole blood since the glucose concentration is quickly obtained. The following problems arise in the use of any of the methods described above.

The blood consists of the serum and the blood cells, and the blood cells contain a liquid component therein. The glucose concentration in the blood cells is the same as that outside the blood cells. A solid component of the blood is contributed by the blood cells. The amount of the solid component is generally 25 to 40% of the blood by volume.

For example, in the case where a whole blood sample is introduced into an isotonic buffer solution and then the glucose concentration is measured, glucose in the blood cells transfers into the buffer solution within about 10 seconds to form an equilibrium state in which the glucose concentration in the buffer solution is the same as that inside the blood cells. In this case, not only the serum of the blood but also the liquid component in the blood cells are diluted with the isotonic buffer solution. Then, all of the glucose in the whole blood is measured. However, a true glucose concentration (in which the solid component in the blood is taken into account) cannot be obtained since the ratio of the blood cell volume to whole blood volume is unknown, thus, the true dilution ratio is unknown. Correction of the concentration was proposed in 1980 by WHO (World Health Organization) by the use of an average ratio of the volume of the blood cells to the whole blood volume (blood cell ratio). However, the ratio of the blood cell volume to whole blood volume is highly variable among individuals. Thus, correction based on an average value introduces a rather large error.

When the First Differential Method is employed, equilibrium is reached within a short time, for example after 2 or 3 seconds from the time the sample is supplied. The glucose concentration measured by this method corresponds to that of the buffer solution which contains not only the glucose in the serum but also a small amount of glucose from the blood cells. Also in this case, the true glucose concentration cannot be obtained since the ratio of the volume of the blood cells to the whole blood volume is unknown. A corrected glucose concentration may be obtained using the average blood cell ratio (hematocrit value). Since the hematocrit value varies among individuals, the corrected glucose concentration includes a rather large error.

In the case where the Second Differential Method is employed, not only the glucose in the serum but also a smaller amount of glucose from the blood cells is measured. It is easily understood that the same problems as arise in the First Differential Method arise in this case.

The amount of glucose which is liberated from the blood cells in the Second Differential Method is less than that in the First Differential Method. Although in the method of the present invention, described below, the First Differential Method or the Second Differential Methods is used, the present method is not affected by the amount of liberated glucose since it is very small and the error is canceled when the measured glucose concentration is converted as described below.

As described above, the Glucose Sensor Method is an effective method to quickly measure the glucose concentration itself. However, the centrifugal separation to obtain the serum cannot be omitted as long as the blood cell volume to whole blood volume ratio is unknown. Therefore, the glucose concentration cannot be measured in the whole blood.

SUMMARY OF THE INVENTION

It is an object of the present invention to provide a method for the quick and accurate determination of the true blood sugar concentration from a measured glucose concentration which is obtained from a whole blood sample by the biosensor method in which the problems caused by the individual variation in blood cell ratio as described above are overcome.

According to the present invention, there is provided a method for the determination of a glucose concentration in a whole blood sample comprising steps of:

1) obtaining two kinds of measured glucose concentrations in a whole blood sample to be measured by "Equilibrium Method" and a method selected from a group consisting of "First Differential Method" and "Second Differential Method", 2) estimating a ratio of blood cell volume to the whole blood volume from a ratio of one measured glucose concentration to the other on the basis of a previously established relation between the blood cell ratio and a function of the ratio of said two measured concentrations, whereby a conversion factor defined as a ratio of a true glucose concentration in the whole blood to the glucose concentration measured by on of said three Methods is obtained, and 3) converting said one measured glucose concentration with the obtained conversion factor to give the true glucose concentration as the glucose concentration in the whole blood.

The "Equilibrium Method", the "First Differential Method" or the "Second Differential Method" is, herein, the same Glucose Sensor Method as described in the background part of the present specification, in which method the combination of the fixed glucose oxidase with the hydrogen peroxide electrode is used.

DETAILED DESCRIPTION OF THE INVENTION

Figure 1:
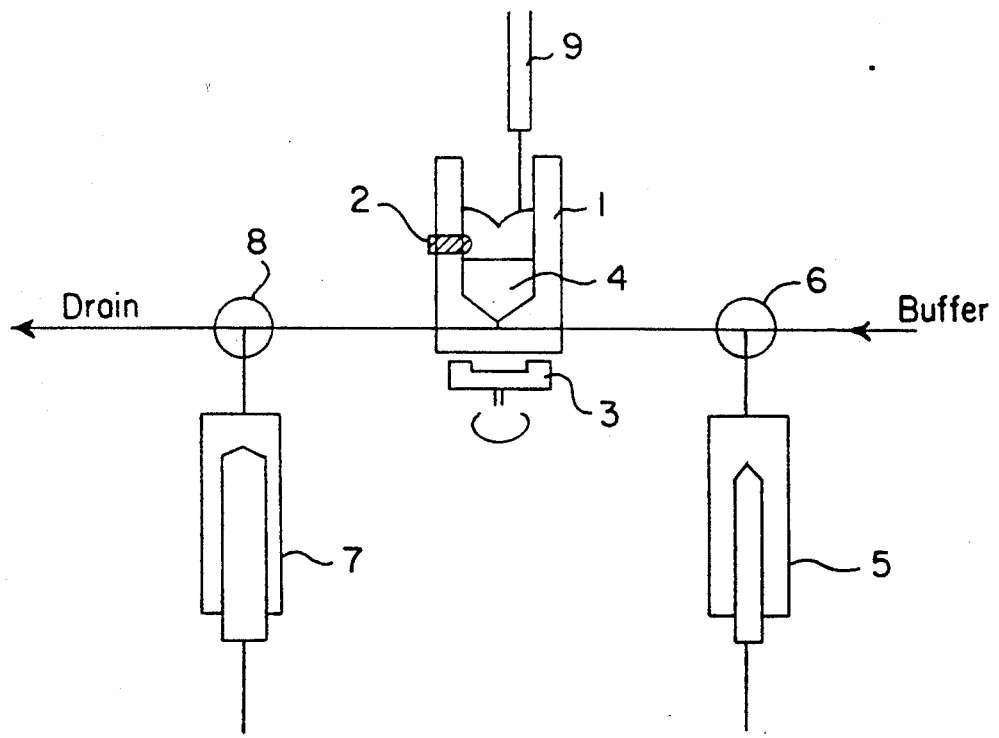
FIG. 1 schematically shows an apparatus with which a method of the present invention is performed by the Glucose Sensor Method.
Figure 2:
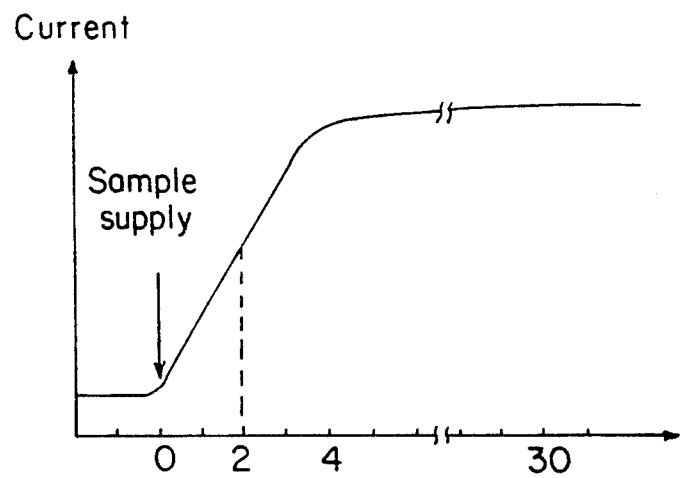
FIG. 2 is a graph showing a curve obtained by Equilibrium Method.
Figure 3:
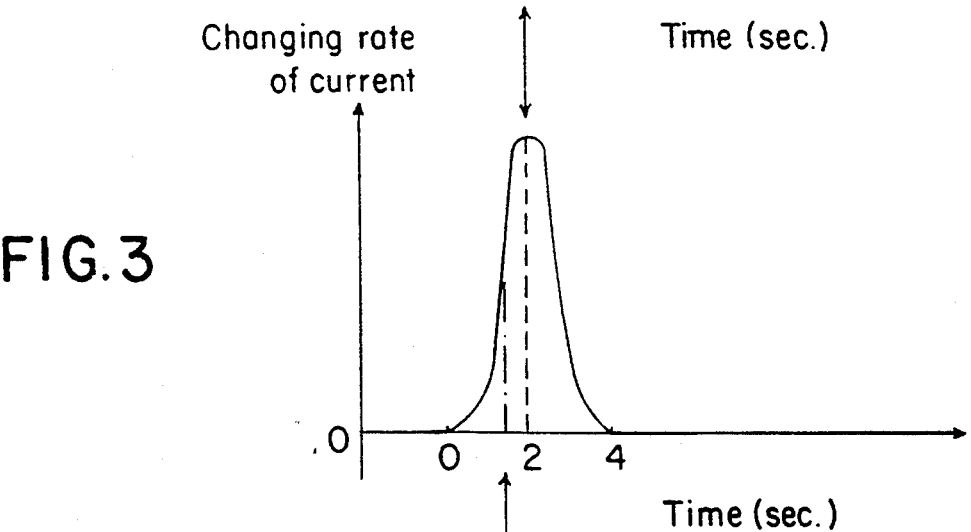
FIG. 3 is a graph showing a curve obtained by First Differential Method.
Figure 4:
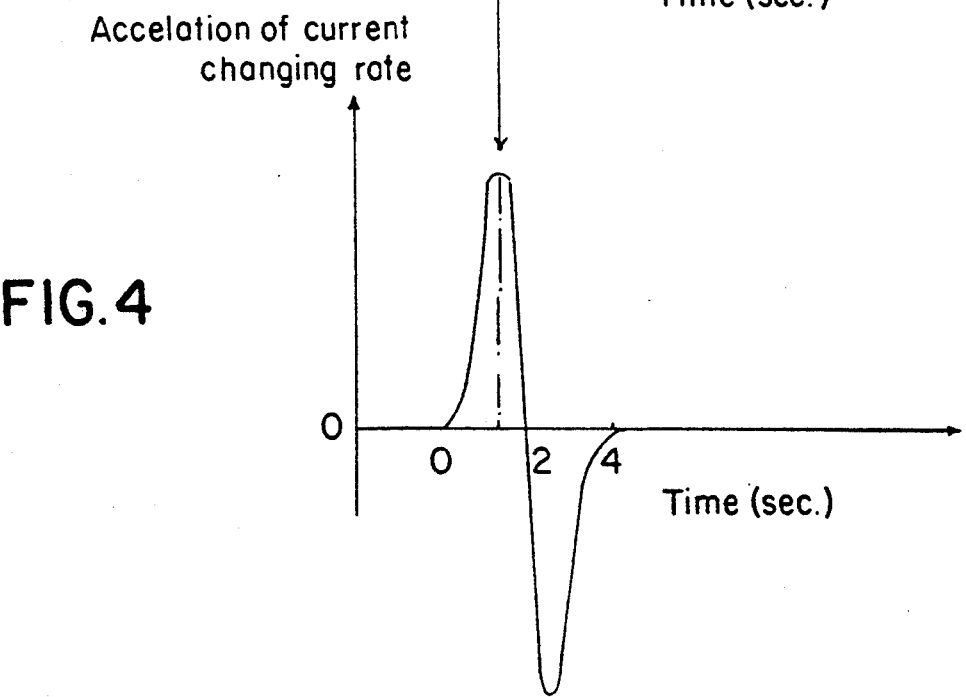
FIG. 4 is a graph showing a curve obtained by Second Differential Method.

The following definitions are used in the description of the invention below:

A = volume of an undiluted whole blood sample.

B = volume of a buffer solution used to dilute a whole blood sample.
a = volume of the solid component of a whole blood sample.
b = volume of the liquid component of the blood cell in the whole blood sample. p1 c = volume of serum component of a whole blood sample.
X = c/A
$C_o$ = true glucose concentration in a sample.
$C_x$ = uncorrected glucose concentration in a sample, measured by the equilibrium method.
$C_y$ = uncorrected glucose concentration in a sample, measured by a differential method.
$R_x = C_x/C_o$.
$R_y = C_y/C_o$.
$\mu = R_x/R_y = C_x/C_y$.

The present invention is completed on the basis of following considerations:

If one of the Glucose Sensor Methods is applied, the measured glucose concentration deviates from the true glucose concentration (i.e. a blood sugar concentration in a liquid component of the blood) since the blood cells (or solid component) are present in the whole blood as described above. Therefore, when the deviation of the measured glucose concentration from the true glucose concentration has been previously known depending on the ratio of the volume of the blood cells (solid component) to the volume of the whole blood, conversely such ratio can be estimated from the deviation extent.

In the case where the blood sugar concentration is determined with the Glucose Sensor Method, a given amount of the whole blood [A] (for example 20 μl) is diluted with a given amount of the buffer solution [B] (for example 1.5 ml). Then, the apparent diluting ratio is equal to (A+B)/A. When the glucose concentration is to be measured in an unseparated blood sample [A], which consists of an amount of the serum [c] and the blood cells consisting of an amount of the solid component [a] and an amount of a liquid component [b] on the basis of volume, i.e. A = a+b+c, the apparent diluting ratio is equal to (A+B)/A but the true diluting ratio is equal to (b+c+B)/(b+c) since glucose in the serum [c] and in the liquid component [b] is to be measured. When there are no blood cells in the blood sample, that is, the sample consists only of the serum, the true diluting ratio is equal to the apparent diluting ratio, as a = 0. Thus, in that case the measured glucose concentration is equal to the true glucose concentration.

When the First Differential Method or the Second Differential Method is applied, glucose only in the serum [c] is measured. Thus, the true diluting ratio is equal to (c+B)/c. Since the solid component in the blood is due to the blood cells, the measured glucose concentration can be converted to the true glucose concentration if the ratio of the volume of the blood cells to whole blood volume is estimated.

According to the present invention, the ratio of the blood cell volume to whole blood volume (i.e. (a+b)/A) or the ratio of the serum volume to whole blood volume (i.e. c/A) is estimated and then the conversion coefficient is obtained as described below. Therefore, the true glucose concentration is obtained by converting the measured glucose concentration with the conversion coefficient.

Now, the method for estimating the blood cell ratio will be described.

Figure 5:
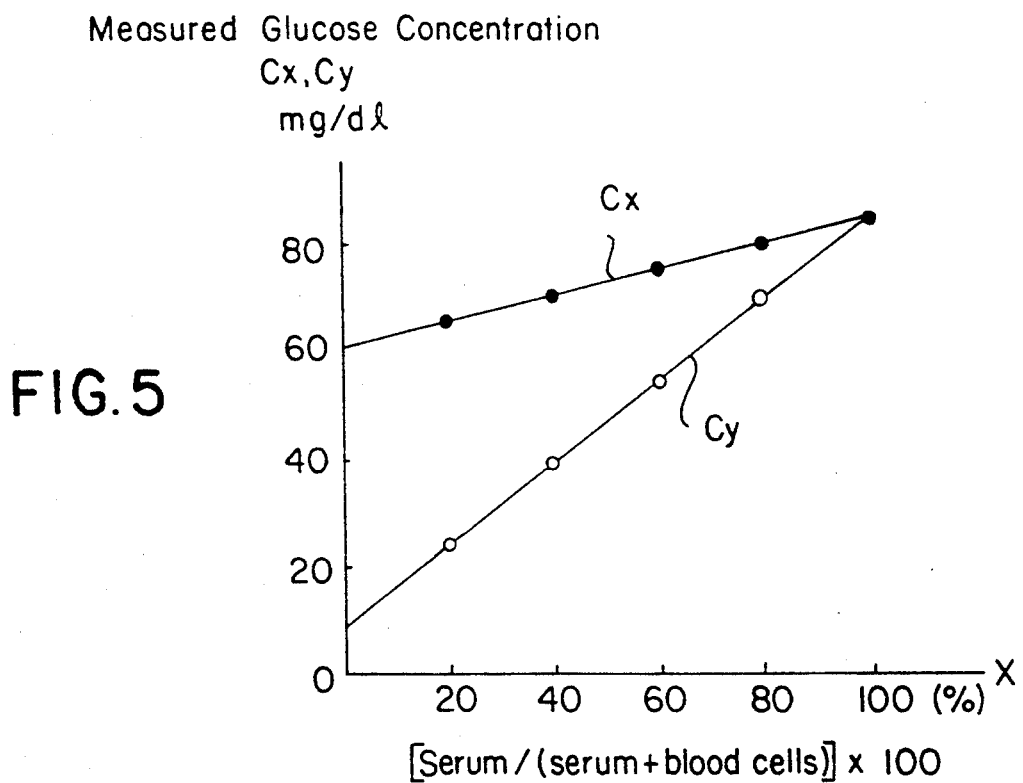
FIG. 5 is a graph showing a relation between a measured glucose concentration [Cx or Cy] and a ratio of serum volume to serum volume plus blood cell volume [X].

A blood sample containing glucose at a certain constant concentration is subjected to the Equilibrium Method while changing the ratio of the blood cells, whereby results as shown in FIG. 5 are obtained. In the graph shown in FIG. 5, the ordinate X indicates [serum/(serum+blood cells)] × 100 (%) on the basis of volume, and the abscissa shows the measured glucose concentration.

It is clearly seen from the graph in FIG. 5 that the measured glucose concentration $C_x$ is smaller than the true glucose concentration (except at X = 100%) since the apparent diluting ratio is not changed in spite of increase of the true diluting ratio when the blood cell ratio increases, that is, [c] decreases, whereby the proportion of the solid component increases.

Then, with respect to the same samples as the $C_x$ values are obtained in the above Equilibrium Method, the measured glucose concentrations are obtained by the First Differential Method, which are shown in terms of $C_y$ in the graph in FIG. 5. In the case whereby the First Differential Method is applied, the relative maximum value of dI/dt is reached before the glucose in the blood cells is released into the buffer solution as described above. Then the glucose concentration is practically measured under the condition that glucose only in the serum is diluted.

Therefore, the measured glucose concentration $C_y$ is smaller than that obtained by the Equilibrium Method, since the true diluting ratio is larger than that in the case of the Equilibrium Method since glucose in the liquid component of the blood cells [b] is not measured. Thus, the apparent diluting ratio is not changed and the amounts of the whole blood sample and the buffer solution are the same as those in the above measurement made using the Equilibrium Method. Therefore, as the blood cell ratio increases, the measured glucose concentration decreases, since the amount of glucose available to be measured that is contributed by the serum decreases because of the decrease of [c while the apparent diluting ratio is not changed in spite of the increase in the true diluting ratio.

Both measured glucose concentrations ($C_x$ and $C_y$) deviate from the true glucose concentration $C_o$ (at X = 100%). The extent of each deviation is $C_x/C_o$ (= $R_x$) in the case of the Equilibrium Method or $C_y/C_o$ (= $R_y$) in the case of the First Differential Method. A ratio (u) of such deviations is as follows:

$$\mu = R_x/R_y = C_x/C_y$$

Thus, with respect to some standard samples each having different known ratio X of an amount of serum to a total amount of blood cells plus serum (X = c/[a+b+c]), $C_x$ and $C_y$ are determined and then a relation between X and μ is obtained as following equation:

$$X = fn(\mu) \tag{1}$$

wherein fn means a function.

When the relations between the measured glucose concentration $C_x$ and X and between the measured glucose concentration $C_y$ and X are expressed by linear relations, respectively, the relation between X and μ is expressed by a hyperbolic relation. If a more accurate relation is required, an approximate expression rather than the hyperbolic relation can be easily obtained by any suitable mathematical technique.

Figure 6:
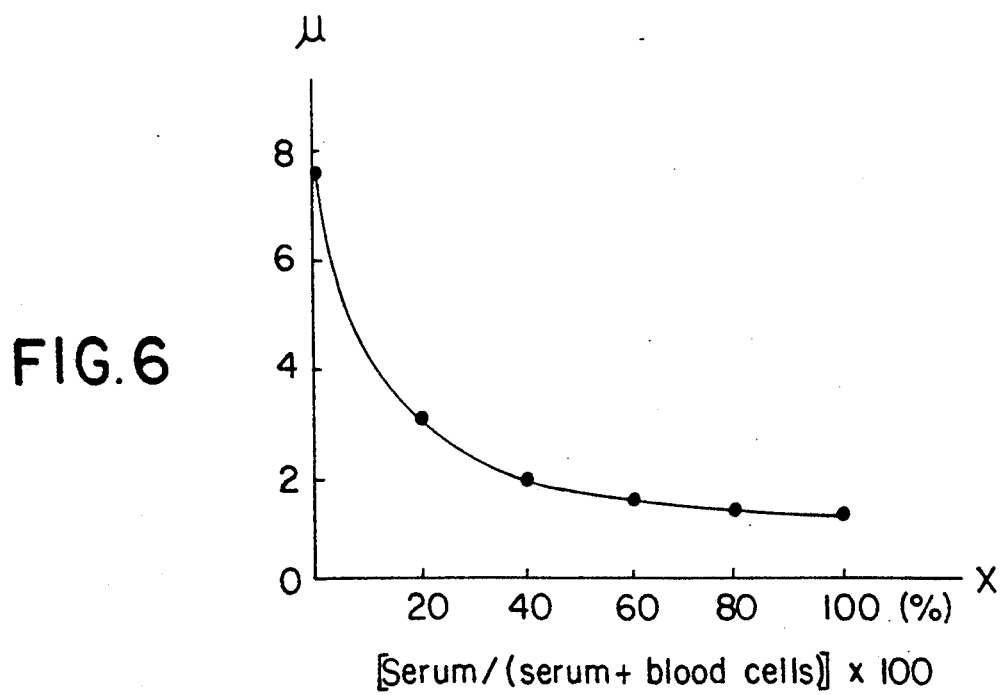
FIG. 6 shows a relation between a measured glucose concentration ratio [$\mu$] and the ratio of the serum volume to the serum volume plus the blood cell volume [X].

The relation between μ and X on the basis of the data as shown in FIG. 5 is indicated in a graph in FIG. 6.

When the relation as indicated in FIG. 6 has been previously known, X is easily estimated by calculating $\mu$ from the data obtained by the Equilibrium Method and the First Differential Method.

In the method of the present invention, Cx and Cy are obtained with respect to a whole blood sample, and then $\mu$ is easily calculated. With the calculated $\mu$, X is estimated from the equation (1) or the same curve as indicated in FIG. 6. When x is estimated, the conversion factor (Co/Cx) at the estimated X can be obtained from the data as shown in FIG. 7.

Since the relation between X and the conversion factor does not depend on the glucose concentration of the sample, such relation only has to be determined once. FIG. 7 is a graph which shows a relation between the logarithm of the conversion factor (a ratio of the glucose concentration in serum [Co] (i.e. the true glucose concentration) to the measured glucose concentration by the Equilibrium Method [Cx]), namely, log [Co/Cx], and the blood cell ratio (i.e. [volume of blood cells/(volume of serum+volume of blood cells)]×100[%]. understood from FIG. 7 that the relation is nearly linear.

Figure 7:
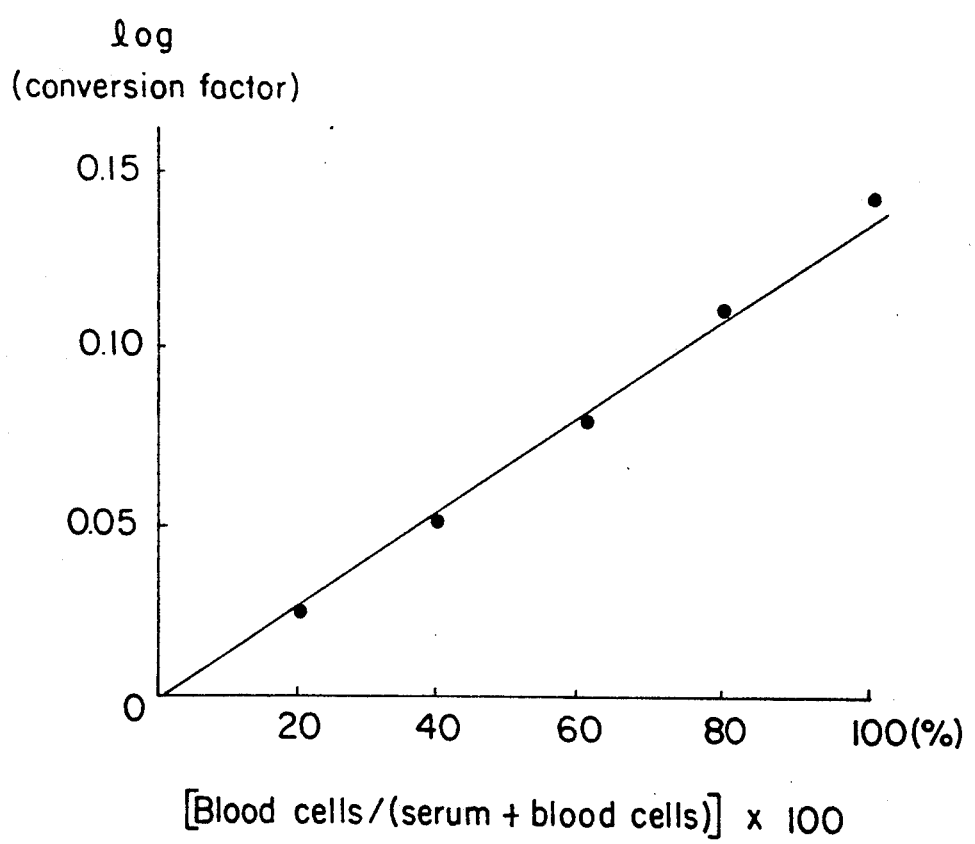
FIG. 7 shows a relation between a conversion factor and the ratio of the blood cell volume to the serum volume plus the blood cell volume [1—X].

From FIG. 7, the conversion factor is obtained. Since the abscissa indicates not the serum ratio but the blood cell ratio the conversion factor is obtained after estimation of the blood cell ratio from X. Then, the true glucose concentration is obtained by multiplying the glucose concentration measured using the Equilibrium Method by the conversion factor. In the case where the glucose concentration measured by the First Differential Method is multiplied, the same procedures as in the case of the Equilibrium Method are carried out except that Co/Cy is used instead of Co/Cx in the estimation of the conversion factor.

In the case where the Second Differential Method is used, the measured glucose concentration is affected by the blood cells as in the First Differential Method. Since the period from the sample supply into the buffer solution to the appearance of the relative maximum value in the Second Differential Method is shorter than that in the First Differential Method, the amount of glucose released from the blood cells is smaller and therefore the effect of the blood cells is more remarkable. However, such effect is proportional to the amount of the blood cells as in the First Differential Method. Thus, when a relation between the blood cell ratio and a ratio of the measured glucose concentration by the Equilibrium Method to the measured glucose concentration by the Second Differential Method has been previously obtained as in the case where the Equilibrium Method and the First Differential Method are used, the true glucose concentration is obtained from a curve as shown in FIG. 7.

Though in the basic principles of the present invention the procedures as described above should be followed, such procedures are easily programmed in software on the basis of the present invention and easily processed with a computer. Thus, when the calibration curve as shown in FIG. 7 has been previously obtained, the glucose concentration can be obtained in real time.

Conventionally, the determination of the glucose concentration has required the separation of the serum from the blood. According to the present invention, the determination of the glucose concentration in whole blood can be performed so that the separation of the serum from the blood is omitted in the determination of the glucose concentration. Thus, the time required for such separation is saved and the overall time for making the determination is remarkably shortened.

EXAMPLE

Preparation

In the example, a commercial apparatus used for the glucose concentration measurement (commercially available as GA-140 from Kyoto Daiichi Kagaku Co., Ltd., Kyoto, Japan) was modified as described below. The apparatus comprised a hydrogen peroxide electrode (commercially available as Type E-08 from Kyoto Daiichi Kagaku Co., ltd.) as a sensor to which a glucose oxidase fixed membrane was installed. To perform the measurement, a blood sample was automatically sucked from a sample cup on a turntable.

For each measurement, 1.7 ml of a buffer solution (phosphoric acid buffer solution of 0.075M, pH=6.7) and 20 $\mu$l of the blood sample were used. The apparatus was originally for the measurement of the glucose concentration by the First Differential Method and it was modified so that the Equilibrium Method was also performed and output data (current) from the hydrogen peroxide electrode was processed through an interface by a personal computer (commercially available as PC9801 from NEC Corp, Tokyo, Japan).

Before the measurement of a blood sample, a standard glucose solution of 150 mg-glucose/dl was subjected to measurements by the Equilibrium Method and the First Differential Method for calibration of each Method.

Then, a blood sample was divided into a blood cell sample and a serum sample by centrifugation. The glucose concentration in the serum sample was measured by the Equilibrium Method and the First Differential Method. The glucose concentration was measured to be 84 mg/dl by each method.

With the use of the serum sample and the blood cell sample which were prepared as described above, standard samples having a percentage of the blood cells by volume of 0, 20, 40, 60, and 80% were prepared and the glucose concentrations thereof were measured. The results on each standard sample by the Equilibrium Method and the First Differential Method are as shown in FIG. 5.

Then, the curve in the graph as shown in FIG. 6 was obtained by the calculation of $\mu$=(the measured glucose concentration by the Equilibrium Method)/(the measured glucose concentration by the First Differential Method) in relation to the percentage of the serum, thus the blood cell ratio. In FIG. 6, the relation is shown in relation to the ratio of the serum volume to the whole blood volume.

FIG. 7 shows the graph which indicates the relation between the logarithm of the converted conversion factor (i.e. the glucose concentration in the serum (=84 mg/dl)/the measured glucose concentration in each standard sample by the Equilibrium Method) and the blood cell ratio.

Measurement of Sample

The glucose concentration in the whole blood was measured with respect to thirty blood samples as follows:

(a) Each sample was divided into two samples.

(b) One of the two divided samples was subjected to the separation by centrifugation, and the glucose concentration in the separated serum was measured by the First Differential Method.

(c) With respect to the other sample of the two divided samples, the glucose concentration was measured in the whole blood by the First Differential Method.

(d) The ratio ($\mu$) was calculated on each sample from the measured glucose concentrations by the Equilibrium Method and the First Differential Method. Then, the percentage of the whole blood volume consisting of the serum [X], thus the blood cell ratio, in the whole blood was also estimated from the curve in FIG. 6.

(e) The conversion factor which corresponds to the estimated blood cell ratio was obtained from FIG. 7 and then the converted glucose concentration was obtained as the true glucose concentration by multiplying the glucose concentration measured by the Equilibrium Method by the conversion factor.

Results

A correlation between the measured glucose concentrations obtained in the step (b) and those obtained in the step (c) was evaluated by plotting the former along X axis and the latter along Y axis. The correlation was such that Y+0.904·X and a correlation coefficient $\gamma = 0.962$.

Similarly, the correlation between the measured glucose concentrations obtained in the step (b) and those obtained in the steps (d and e) was evaluated by plotting the former along the X axis and the latter along the Y axis. The correlation was such that Y=0.998·X and the correlation coefficient $\gamma = 0.995$.

Although the present invention has been described with reference to the above example, various modifications may be made within the concept of the present invention. For example, an oxygen electrode or a FET (field effect transistor) can be used as a sensor instead of the hydrogen peroxide electrode. The enzyme need not be fixed to the electrode but rather it may be present in the buffer solution. Further, although the First Differential method and the Second Differential Method are described in relation to the present invention in which a differentiation is used for the determination of the glucose concentration, a higher order differentiation can be applied to the determination of the glucose concentration.

What is claimed is:

1. A method for the in vitro measurement of the concentration of glucose in a whole blood sample, which comprises:

A) obtaining a calibration curve relating (a) a conversion factor, defined as the ratio of the measured glucose concentration in a whole blood sample to the measured glucose concentration of the serum from said whole blood sample to (b) the proportion of the whole blood volume that consists of the serum fraction;

B) creating a calibration curve relating (a) the ratio of glucose concentration in said whole blood sample measured before glucose has diffused out of the cells into a solution used to dilute said whole blood sample to the glucose concentration measured in said whole blood sample after glucose has diffused out of the cells into said solution to (b) the proportion of the whole blood volume that consists of the serum fraction;

C) diluting a whole blood sample in which the glucose concentration is to be determined in a solution suitable for measuring glucose concentration;

D) obtaining a first value (Cy) of the concentration of glucose in the sample solution of step (C) before the glucose contained within the cells has diffused out of the cells into the solution used to dilute the sample;

E) obtaining a second value (Cx) of the concentration of glucose in the sample solution of step (C) after the glucose contained within the cells has diffused out of the cells into the solution used to dilute the sample;

F) obtaining the ratio of Cx/Cy from the values obtained in steps (D) and (E);

G) estimating the proportion of the whole blood volume of said whole blood sample of step (C) which consists of the serum fraction (X) by reference to the calibration curve obtained in step (B);

H) obtaining the value for the conversion factor at the value of X determined in step (G) by reference to the calibration curve obtained in step (A); and I) determining the concentration of glucose in the whole blood sample of step (C) by multiplying the value of Cx obtained in step (E) by the value of the conversion factor obtained in step (H).

2. A method for the in vitro measurement of the concentration of glucose in a whole blood sample, which comprises:

A) obtaining whole blood sample and separating it into the serum and cellular fractions;

B) mixing the separated fractions of step (A) in varying proportions;

C) diluting the samples obtained from step B) in a vessel with a solution suitable for measuring the glucose concentration in the diluted sample;

D) obtaining a first value of the concentration of glucose in each of said diluted samples before the glucose contained within the cells has diffused out of the cells into the solution used to dilute the sample (Cy);

E) obtaining a second value of the concentration of glucose in each of said diluted samples after the glucose contained within the cells has diffused out of the cells into the solution used to dilute the sample (Cs);

F) creating a calibration curve relating the proportion of the whole blood sample which comprises the serum fraction (X) to the ratio of the value of step (E) to the value of step (D) (Cx/Cy);

G) creating a calibration curve relating the conversion factor (Co/Cx), said conversion factor being the ratio of Cx when X is 100% (Co) to the Cx obtained at variable values of X to the proportion of the whole blood volume which consists of the volume of the cellular fraction (1−X);

H) obtaining a whole blood sample in which the glucose concentration is to be determined;

I) diluting said whole blood sample in a solution suitable for the measurement of glucose concentration in said diluted sample;

J) obtaining a first value of the concentration of glucose in the sample solution obtained in step (I) before the glucose contained within the cells has diffused out of the cells into the solution used to dilute the sample;

K) obtaining a second value of the concentration of glucose in the sample solution obtained in step (I) after the glucose contained within the cells has diffused out of the cells into the solution used to dilute the sample;

L) obtaining the ratio of Cx/Cy from the values obtained in steps J) and K);

M) estimating the proportion of the whole blood volume in the whole blood sample of step (H) which consists of the serum fraction (X) by reference to the calibration curve obtained in step F);

N) obtaining the value of the proportion of whole blood volume in the whole blood sample of step (H) which consists of the volume of the cellular fraction by the ration $1-X$;

O) obtaining the value for the conversion factor at the value of $1-X$ determined in step (N) by reference to the calibration curve obtained in step (G): and P) determining the concentration of glucose in the whole blood sample of step (H) by multiplying the value of Cx obtained in step (K) by the value of the conversion factor obtained in step (O).

3. The method of claim 2, wherein the values in steps E and K are obtained by:

EK1) diluting a standard solution of known glucose concentration in said solution suitable for measuring the glucose concentration;

EK2) measuring the value of the current output of an electrode, after the current output has reached steady state, as a function of glucose concentration in said diluted standard solution to obtain a calibration curve relating electrode current and glucose concentration; and EK3) measuring the glucose concentration in the blood samples by measuring the output current of the electrode and referring to the calibration curve obtained in step EK2;

and wherein the measurements made in steps D and J are obtained by:

DJ1) diluting a standard solution of known glucose concentration in said solution suitable for measuring glucose concentration;

DJ2) measuring the maximum value of the first derivative with respect to time of the output current of the electrode as a function of glucose concentration in said diluted standard solution to obtain a calibration curve relating said maximum value of the first derivative and glucose concentration; and DJ3) measuring the glucose concentration in the blood samples by measuring the maximum value of said first derivative and referring to the calibration curve in step (DJ2).

4. The method of claim 3, wherein the calibration curve in step (DJ2) is made and the value of Cy is measured using teh maximum value of the second, or higher derivative with respect to time of the output current of the electrode 5. The method of claim 3, wherein the electrode is an oxygen electrode or a hydrogen peroxide electrode or a field effect transistor.

6. The method of claim 5, wherein said electrode is operatively linked so as to measure the rate of a glucose oxidase enzymatic reaction.

7. The method of claim 6, wherein said glucose oxidase enzyme is immobilized on a membrane surface.

8. A method for the measurement of the concentration of glucose in a whole blood sample, by means of a hydrogen peroxide electrode (HPE) the output of which is a function of the progress of a glucose oxidase enzymatic reaction occurring in a vessel, which comprises:

A) diluting a standard solution of defined glucose concentration in a buffer in a reaction vessel containing glucose oxidase and a HPE, and obtaining a calibration curve relating the current of the HPE, measured when the rate of hydrogen peroxide production has reached a steady state, to the concentration of glucose;

B) diluting a standard solution of defined glucose concentration in said buffer in said reaction vessel, and obtaining a calibration curve relating the maximum value of the first derivative with respect to time of the current of the HPE to the concentration of glucose;

C) obtaining a whole blood sample and separating it into the serum and cellular fractions;

D) mixing the separated fractions of step (C) in varying proportions to form a series of reconstituted whole blood samples;

E) diluting the samples obtained from step (D) in a buffer suitable for measuring the glucose concentration in the diluted sample;

F) obtaining a first reading in each of the diluted samples of step (E), of the current generated by the HPE, after the rate of hydrogen peroxide production has reached a steady state, then converting said first reading into a first measurement of the glucose concentration in said diluted samples of step (E) by reference to the calibration curve obtained in step (A), the value of said measurement being called Cx;

(G) obtaining a second reading in each of the diluted samples of step (E), of the maximum value of the first derivative with respect to time, of the current generated by the HPE, then converting said second reading into a second measurement of the glucose concentration in said diluted samples of step (E) by reference to the calibration curve obtained in step (B), the value of said measurement being called Cy;

H) creating a calibration curve relating the proportion of the whole blood sample which comprises the serum fraction (X) to the ratio of the measurement of step (F) to the measurement of step (G) (Cx/Cy);

I) creating a calibration curve relating the conversion factor (Co/Cx), said conversion factor being the ratio of Cx when X is 100% (Co) to the Cx obtained at variable values of X, to the proportion of the whole blood volume which consists of the volume of the cellular fraction $(1-X)$;

J) obtaining a whole blood sample in which the glucose concentration is to be determined and diluting said whole blood sample with said buffer in said reaction vessel;

K) obtaining a first reading in said whole blood sample of step (J), of the current generated by the HPE, after the rate of hydrogen peroxide production has reached a steady state, then converting said first reading into a first measurement of the glucose concentration in said whole blood sample by reference to the calibration curve obtained in step (A), the value of said measurement being called Cx;

L) obtaining a second reading in said whole blood sample of step (J), of the maximum value of the first derivative with respect to time, of the current generated by the HPE, then converting said second reading into a second measurement of the glucose concentration in said whole blood sample by reference to the calibration curve obtained in step (B), the value of said measurement being called Cy;

M) estimating the fraction of the whole blood volume in the whole blood sample of step (J) that consists of the serum volume (X) by reference to the calibration curve obtained in step (H);

N) estimating the fraction of the whole blood volume in the whole blood sample of step (J) that consists of the blood cell volume by the relationship, $1-(X)$;

O) determining a conversion factor (Co/Cx) by reference to the calibration curve obtained in step (I); and P) multiplying said first measurement of step (K), Cx, by the conversion factor obtained in step (O) to obtain the value of the true glucose concentration in the whole blood of step (J), Co.

9. The method of claim 8, wherein the calibration curve in step (B) is made and the value of Cy is measured using the maximum value of the second, or higher, derivative with respect to time of the current of the HPE.

10. The method of claim 8, wherein the glucose oxidase is immobilized as part of the hydrogen peroxide electrode.

11. The method of claim 8, wherein the HPE is replaced by an oxygen electrode or field effect transistor as the sensor.

* * * * *